United States Patent
Mendoza et al.

(10) Patent No.: US 10,176,538 B2
(45) Date of Patent: Jan. 8, 2019

(54) METHOD OF MANAGING PETRO-CHEMICAL RESERVOIR PRODUCTION AND PROGRAM PRODUCT THEREFOR

(71) Applicants: Repsol, S.A., Madrid (ES); International Business Machines Corporation, Armonk, NY (US)

(72) Inventors: Pablo Enrique Vargas Mendoza, Madrid (ES); Jose Maria Segura Serra, Madrid (ES); Nubia Aurora Gonzalez Molano, Madrid (ES); Mookanahallipatna Ramasesha Lashmikantha, Madrid (ES); Roberto Federico Ausas, Sao Carlos (BR); Freddy Ernesto Mackay Espindola, Rio de Janeiro (BR); Carmen Nilda Mena Paz, Ipanema (BR); Eduardo Rocha Rodrigues, Sao Paulo (BR); Paula Aida Sesini, Copacabana (BR)

(73) Assignees: REPSOL, S.A., Madrid (ES); International Business Machines Corporation, Armonk, NY (US)

( * ) Notice: Subject to any disclaimer, the term of this patent is extended or adjusted under 35 U.S.C. 154(b) by 620 days.

(21) Appl. No.: 14/754,929

(22) Filed: Jun. 30, 2015

(65) Prior Publication Data

US 2016/0140674 A1    May 19, 2016

(30) Foreign Application Priority Data

Nov. 17, 2014 (EP) .................................... 14382455

(51) Int. Cl.
*G01V 1/48* (2006.01)
*G06Q 50/02* (2012.01)
(Continued)

(52) U.S. Cl.
CPC .......... *G06Q 50/02* (2013.01); *G01N 33/241* (2013.01); *G01V 99/00* (2013.01);
(Continued)

(58) Field of Classification Search
CPC combination set(s) only.
See application file for complete search history.

(56) References Cited

U.S. PATENT DOCUMENTS 7,617,051 B2    11/2009    Sayers et al.
7,707,018 B2 *    4/2010    Shaw .................... E21B 49/006
                                            703/10

(Continued)

FOREIGN PATENT DOCUMENTS

JP    2004021883 A    1/2004
WO    2014142976       9/2014

OTHER PUBLICATIONS

Matthai, Stephan Konrad, Andrey A. Mezentsev, and Mandefro Belayneh. "Finite element-node-centered finite-volume two-phase-flow experiments with fractured rock represented by unstructured hybrid-element meshes." SPE Reservoir Evaluation & Engineering 10, No. 06 (2007): 740-756.*

(Continued)

*Primary Examiner* — Aniss Chad
(74) *Attorney, Agent, or Firm* — Law Office of Charles W. Peterson, Jr.; Louis J. Percello, Esq.

(57) ABSTRACT

A method and computer program product for managing hydrocarbon field production, e.g., petro-chemical reservoir production. The hydrocarbon field is modeled using the finite volume method (FVM) model and the finite element method (FEM). Centroids are located in each FVM cell and each FEM element and overlapping cells are identified. After determining the distance between centroids for overlapping cells, fluid characteristics are mapped to the FEM
(Continued)

element centroids, weighted inversely for distance between the respective centroids. A permeability/conductivity weighted average is determined for pore pressure and temperature of sub-volumes clustered around each FEM element node. Field production may be adjusted in response to FEM element node characteristics.

11 Claims, 10 Drawing Sheets

(51) Int. Cl.
G01V 99/00 (2009.01)
G06F 17/50 (2006.01)
G06Q 10/06 (2012.01)
G01N 33/24 (2006.01)

(52) U.S. Cl.
CPC ....... G06F 17/5018 (2013.01); G06Q 10/067 (2013.01); G01V 2210/624 (2013.01); G01V 2210/66 (2013.01)

(56) References Cited

U.S. PATENT DOCUMENTS

| | | | |
|---|---|---|---|
| 8,200,464 B2 | 6/2012 | Slavik | |
| 8,255,195 B2* | 8/2012 | Yogeswaren | E21B 49/00 702/6 |
| 8,280,709 B2 | 10/2012 | Koutsabeloulis et al. | |
| 8,423,337 B2 | 4/2013 | Hsu et al. | |
| 8,463,586 B2* | 6/2013 | Mezghani | G01V 99/00 345/420 |
| 9,134,454 B2* | 9/2015 | Mishev | G06F 17/5018 |
| 2012/0136636 A1* | 5/2012 | Kleine | G01V 99/005 703/2 |
| 2013/0030782 A1 | 1/2013 | Yogeswaren | |
| 2013/0035913 A1 | 2/2013 | Mishev et al. | |
| 2013/0138410 A1 | 5/2013 | Yogeswaren | |
| 2013/0166264 A1* | 6/2013 | Usadi | G06F 17/5009 703/2 |
| 2013/0218538 A1* | 8/2013 | Fuecker | G06F 17/5018 703/2 |
| 2013/0231907 A1 | 9/2013 | Yang et al. | |
| 2013/0282348 A1 | 10/2013 | Liu | |
| 2014/0163901 A1 | 6/2014 | Sesini et al. | |
| 2014/0270394 A1 | 9/2014 | Fredrich et al. | |

OTHER PUBLICATIONS

Yang, Junzheng, Xugang Wang, Honglan Zou, and Guoping Liang. "A Combined Finite-Element and Finite-Volume Method in Reservoir Simulation." In Software Engineering (WCSE), 2010 Second World Congress on, vol. 2, pp. 325-328. IEEE, 2010.*
Geiger, Sebastian, Stephen Roberts, S. K. Matthäi, Christopher Zoppou, and A. Burri. "Combining finite element and finite volume methods for efficient multiphase flow simulations in highly heterogeneous and structurally complex geologic media." Geofluids 4, No. 4 (2004): 284-299.*
R. H. Dean, X. Gai, C. M. Stone, and S. Mikoff, A Comparison of techniques for coupling porous flow and Geomechanics, SPE 79709 presented at the Reservoir Symposium, Houston (2003).
Tran D., Buchanan L., and Nghiem L., Improved Gridding Technique for Coupling Geomechanics to Reservoir Flow, Mar. 2010 SPE Journal.
Capasso, G. and Mantica, S. 2006. Numerical Simulation of Compaction and Subsidence Using ABAQUS. In Proceedings of the ABAQUS User's Conference, Cambridge, USA, May 2006.
Susan E. Minkoff, C. Mike Stone, Steve Bryant, Malgorzata Peszynska, Mary F. Wheeler, Coupled fluid flow and geomechanical deformation modeling Journal of Petroleum Science and Engineering 38 (2003) 37-56.
Wellman, G.W., 1999. MAPVAR—a computer program to transfer solution data between finite element meshes. Technical Report, SAND99-0466, Sandia National Labs, Albuquerque, NM.
Mello U. T., Rodrigues J. R. P., Rossa A. L., A control-volume finite-element method for three dimensional multiphase basin modeling, Marine and Petroleum Geology 26 (2009) 504-518.
Lam, N.S-N. 1983. Spatial Interpolation Methods: A Review. Cartography and Geographic Information Science 10 (2): 129-150.
EPSR dated Apr. 5, 2015 for the EP counterpart to this application, Application No. 14382455.

* cited by examiner

METHOD OF MANAGING PETRO-CHEMICAL RESERVOIR PRODUCTION AND PROGRAM PRODUCT THEREFOR

CROSS REFERENCE TO RELATED APPLICATION

The present application claims priority under 35 USC § 119 to European Patent Application No. EP14382455.5, "METHOD OF MANAGING PETRO-CHEMICAL RESERVOIR PRODUCTION AND PROGRAM PRODUCT THEREFOR" to Vargas Mendoza et al., filed Nov. 17, 2014 with the Spanish Patent Office, assigned to the assignees of the present invention and incorporated herein by reference.

BACKGROUND OF THE INVENTION

Field of the Invention

The present invention is related to managing hydrocarbon field production, and especially related to managing energy production from petro-chemical reservoirs.

Background Description

Efficiently extracting energy producing resources from a hydrocarbon reservoir field requires accurately modeling the reservoir to form a comprehensive development plan tailored for the field. The development plan provides production guidelines for a given planning horizon on a drilling schedule selected for the field to maximize production for the reservoir. A reservoir development engineer extracts information from the model for decision makers. Decision makers select a development plan for economically committing limited resources to achieve an optimum return. Whether developing a single well, or for improving production from a world-class reservoir, the required level of analysis can be significant and costly. This is exacerbated by a typically wide range of production choices, such as may be encountered with changing standard business practices or when changing a major investment strategy.

Typical state of the art field simulators used for modeling the reservoir typically models reservoir fluid characteristics, e.g., pore pressure and/or temperature, and geomechanical characteristics separately to approach realistic, reliable results. Throughout the course of reservoir production, fluid properties as well as geomechanical behavior stress the reservoir, change the structure and cause rock deformations. For example, reservoir rock may compact abruptly, pore can partially or completely clog reducing flow, or pore can collapses all together. This can cause ground surface subsidence, damage well casings, consequently, slowing or inhibiting extraction. Temperature affects the rock formation and hydrocarbon material properties, e.g., changing material viscosity. Thus, geomechanical behavior has a significant physical impact on reservoir production.

Consequently, efficiently managing production requires modeling a reservoir both for fluid flow and mechanical responses for structurally behavior. Typically, a reservoir engineer models reservoir fluidically with a finite volume method (FVM) model, where the reservoir is segmented into an array or grid of "finite volumes" each surrounding a central node or centroid. The reservoir engineer models structural rock deformation in a finite element method (FEM) model, where the typically, irregularly-shaped reservoir field is sub-divided into a mesh of smaller, more basic geometric elements, e.g., cubes, cones, and etc., that may vary in size and shape. Planners couple and correlate results between the FEM and FVM models to estimate and extract production potential and economic performance. Thus, coupling FVM and FEM results is a fundamental requirement for petroleum production modeling.

However, because these two models may have very different cells and be very different meshes, coupling FVM and FEM results may be problematic. State of the art pore pressure/temperature projection simulation couples data between the models based solely on geometric and mathematical considerations. Typical state of the art coupling approaches iteratively map model characteristics between models until the mapping converges on an acceptable solution. However, the different grid geometries make coupling the data between the two different grids extremely challenging, often failing to converge on an acceptable solution.

Thus, there is a need for accurately mapping fluid and structural/geomechanical data between different, incompatible FVM grids and FEM meshes, and especially for quickly converging on an acceptable solution to arrive at realistic results with reduced computational cost.

SUMMARY OF THE INVENTION

The present invention relates to a method and computer program product for managing hydrocarbon field production, e.g., petro-chemical reservoir production. The hydrocarbon field may be modeled for fluid flow using the finite volume method (FVM) model and for rock deformations using the finite element method (FEM). Centroids are located in each FVM cell and each FEM element and cells that overlap each element are identified. After determining the distance between centroids for overlapping cells, fluid characteristics are mapped to the FEM element centroids, weighted inversely for distance between the respective centroids. In an inverse volume weighting, a weighted average pore pressure/temperature are projected from the cell centroids to the FEM element nodes. Field production may be adjusted in response to FEM element node characteristics.

BRIEF DESCRIPTION OF THE DRAWINGS

The foregoing and other objects, aspects and advantages will be better understood from the following detailed description of a preferred embodiment of the invention with reference to the drawings, in which.

DESCRIPTION OF PREFERRED EMBODIMENTS

Figure 1A:
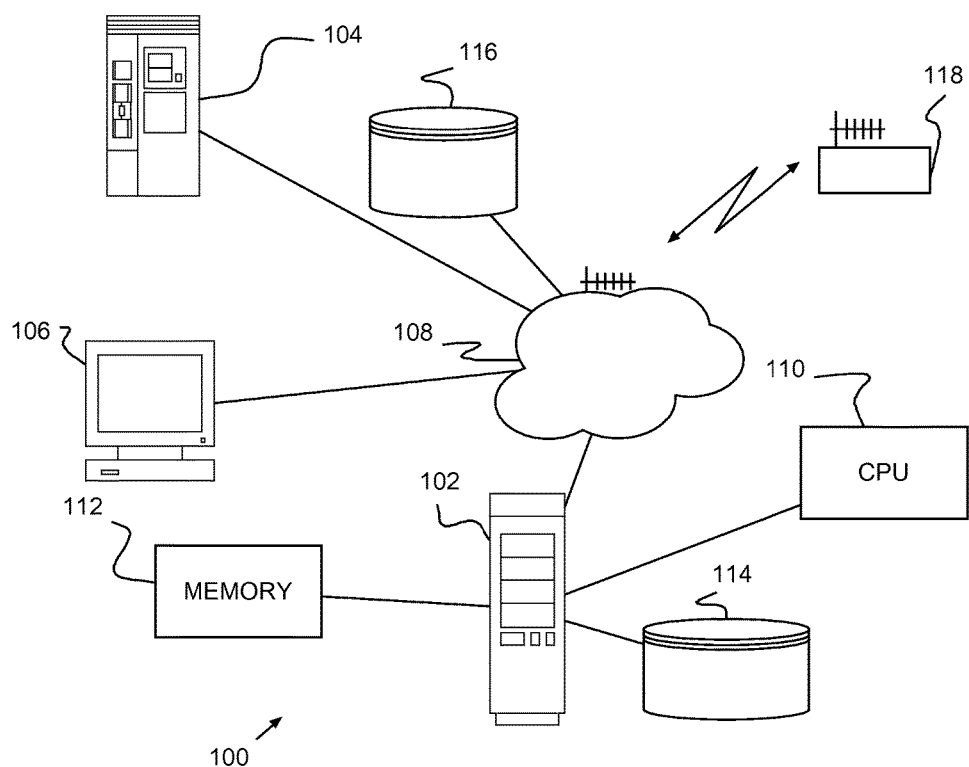
FIGS. 1A-B show an example of a hydrocarbon production system, e.g., for accurately mapping fluid and geomechanical data between different models, according to a preferred embodiment of the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1B:
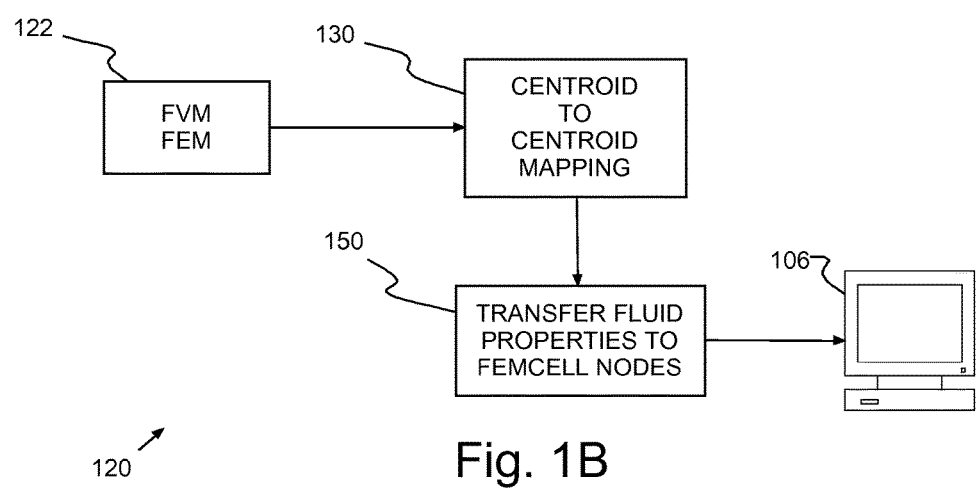

Turning now to the drawings and more particularly, FIGS. 1A-B show an example of a hydrocarbon production management system 100, e.g., accurately mapping 120 fluid and geomechanical data between different models for managing hydrocarbon field production, according to a preferred embodiment of the present invention. Preferably, the hydrocarbon production management system 100 includes single computer, e.g., 102, modeling and mapping fluid and geomechanical data between different representative space, to combine information in otherwise potentially incompatible finite volume method (FVM) grid cells and finite element method (FEM) mesh elements representing the same hydrocarbon field or reservoir.

Although described with a single computer 102, the preferred system may include multiple computers 102, 104, 106 (3 in this example) networked 108 wired or wirelessly, coupled to, and communicating with, each other, and with the method steps 122, 130, 150 on a single one of, or distributed among, the connected computers 102, 104, 106. The network 108 may be, for example, a local area network (LAN), wired or wireless (e.g., Wi-Fi), the Internet, an intranet or a combination thereof. Typically, each of the computers 102, 104, 106 include one or more processors, e.g., a central processing unit (CPU) 110, memory 112 and local non-volatile storage 114. The system 100 may include additional storage, e.g., network attached storage (NAS) 116, and sensors 118 remotely collecting reservoir production data, e.g., from production activity, and passing collected data over the network 108 to the computers 102, 104, 106.

The preferred system 100 couples a FVM model of a reservoir and an FEM model of the reservoir in a, primarily, 2 step coupling 120, projecting pore pressure/temperature from the cell centroids to the FEM element nodes. Preferably, the pore pressure/temperature projections are weighted averages, e.g., weighted for average permeability/conductivity and by an inverse volume (a "beta weighting") factor. Preferably also, the inverse volume is based on sub-volumes clustered around each node. Other suitable beta weighting factors include, for example, inverse distance and volume average. Further, although described herein as mapping from fluid flow (FVM cells) to the geomechanics (FEM elements), it is understood that this is for example only.

Preferably, the hydrocarbon production system 100 begins with modeling 122 the reservoir using both a FEM model and a FVM model. Then, the system 100 maps 130 data between of the reservoir finite volume (FVM grid block or cube) centroids and geomechanics finite element (FEM tetrahedral or hexahedral element) centroids. In particular, the system 100 maps reservoir characteristics at FVM mesh element centroids to FEM mesh element centroids 130 in an inverse-distance weighted transfer, correlating fluid parameter data at the FVM mesh centroids and the FEM mesh centroids. Next, the preferred system 100 maps 150 data from the FEM element centroids to FEM element nodes in a pore pressure/temperature volume-average projection, weighted by permeability/conductivity, averaging pore pressure and temperature projection around FEM mesh nodes, weighted by permeability (k) and conductivity (λ) for each sub-volume around each node.

Figure 2:
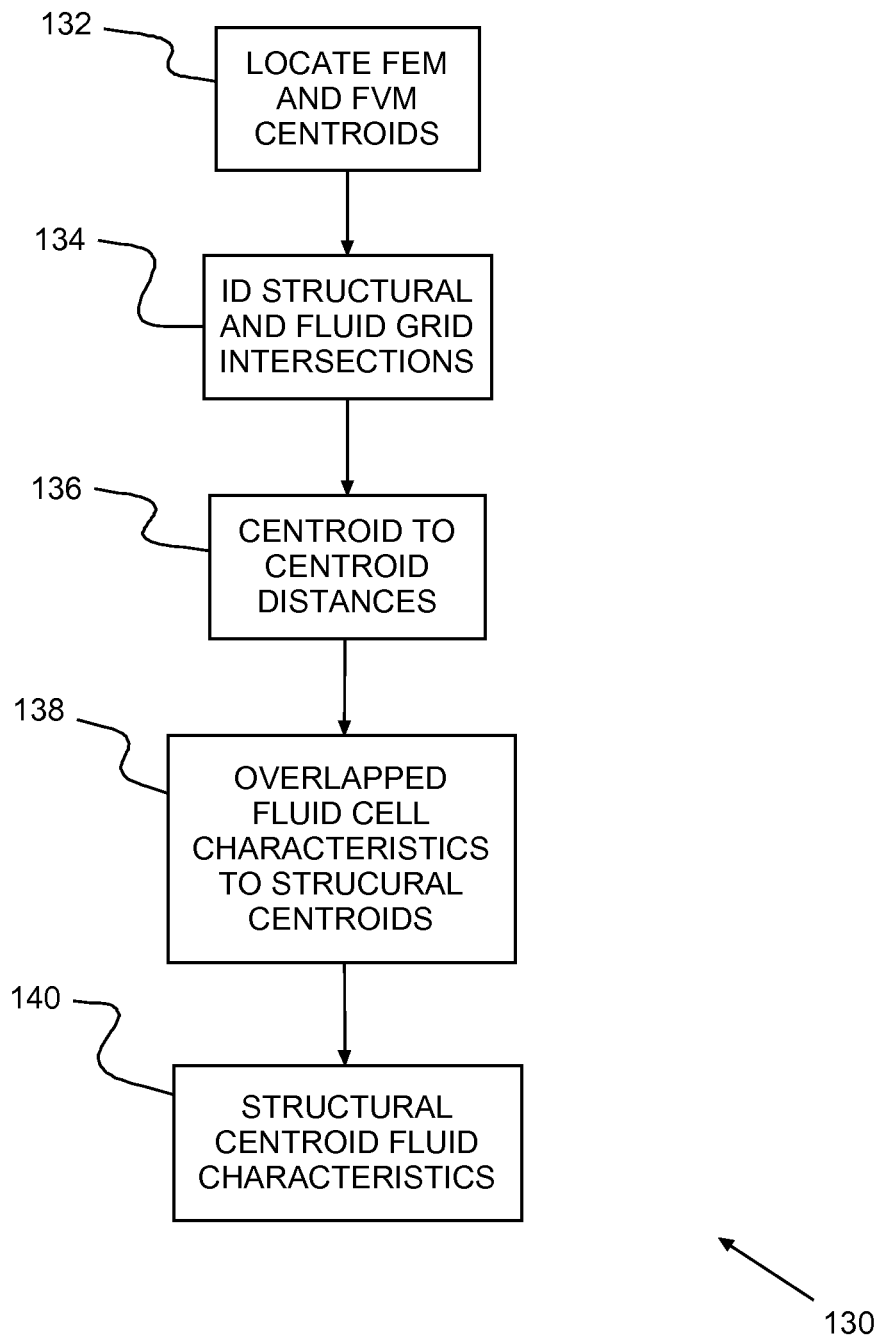
FIG. 2 shows an example of steps in centroid to centroid mapping for a modeled reservoir by a preferred system.

FIG. 2 shows an example of centroid to centroid mapping 130 for a modeled 122 reservoir by a preferred system 100 with reference to FIGS. 1A-B. Centroid to centroid mapping 130 begins with locating 132 all cell centroids for both the FVM grid and FEM mesh. Then, identifying 134 all FVM cells overlapping FEM elements; the system 100 determines 136 for each overlapped/overlapping cell the distance between overlapping FVM cell centroids and the respective overlapped FEM element centroids. The system 100 maps 138 fluid flow characteristics from the overlapping FVM cells to the respective overlapped FEM element centroids. For example, the system 100 maps 138 pore pressure and diagonal permeability tensors to the FEM element centroids. Simultaneously, the system 100 determines the permeability norm at FEM centroids, for the permeability norm $\|k\| = \sqrt{(k_{xx})^2 + (k_{yy})^2 + (k_{zz})^2}$. Finally, the system 100 projects 140 FEM element centroid characteristics in an inverse-distance weighted determination to FEM element nodes. For example, the system 100 may determine pressure and permeability norm at each FVM centroid relating to the identified FEM element centroids, e.g., using a typical inverse-distance weighted approach.

FIGS. 3A-D show examples of 2 dimensional (2D) and 3D (in exploded view) modeled reservoirs 200, 220, 240, 260 modeled with FVM grids 202, 222, 242, 262 overlapping an FEM mesh 212, 232, 252, 272 in step 122 of FIG. 1B. Each FVM grid 202, 222, 242, 262 includes an array or grid of regular cells, 204, 224, 244, 264, rectangular/square or cubic in these examples. Each FEM mesh 212, 232, 252, 272 includes irregular shaped 2D or 3D elements, 214, 234, 254, 274. Centroid to centroid mapping 130 begins by locating 132 the centroids 206, 226, 246, 266 in each FVM cell, 204, 224, 244, 264; and, locating 132 the centroids 216, 236, 256, 276, 310 in each FEM element 214, 234, 254, 274.

Figure 3A:
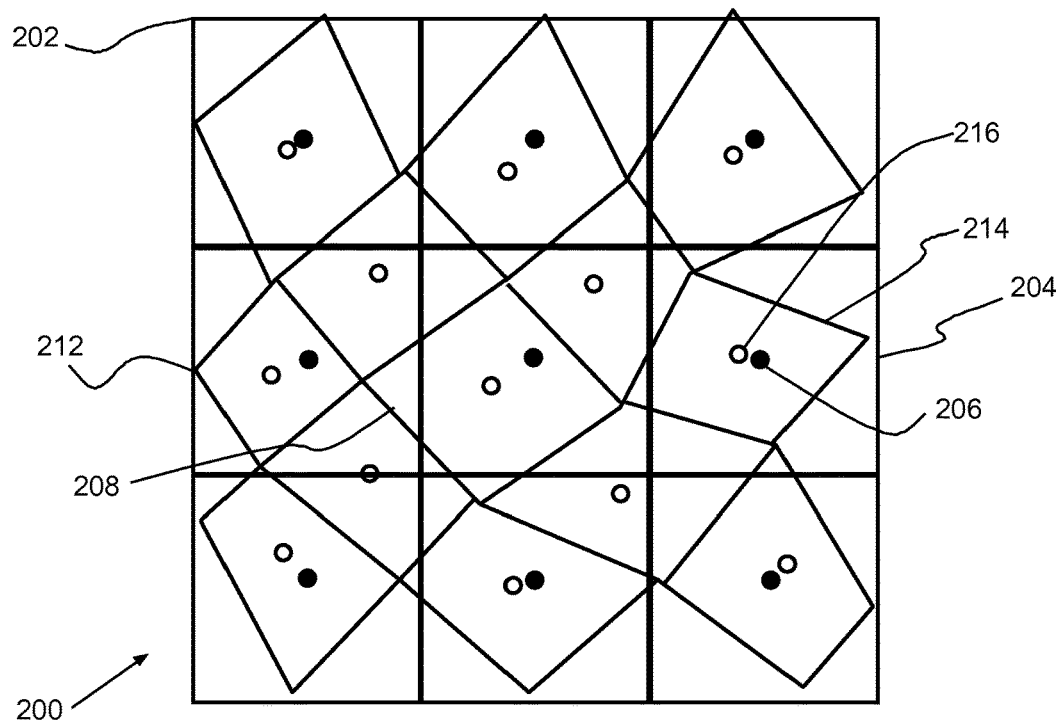
FIGS. 3A-D show examples of 2 dimensional (2D) and 3D (in exploded view) modeled reservoirs modeled with FVM grids overlapping an FEM meshes.
Figure 3B:
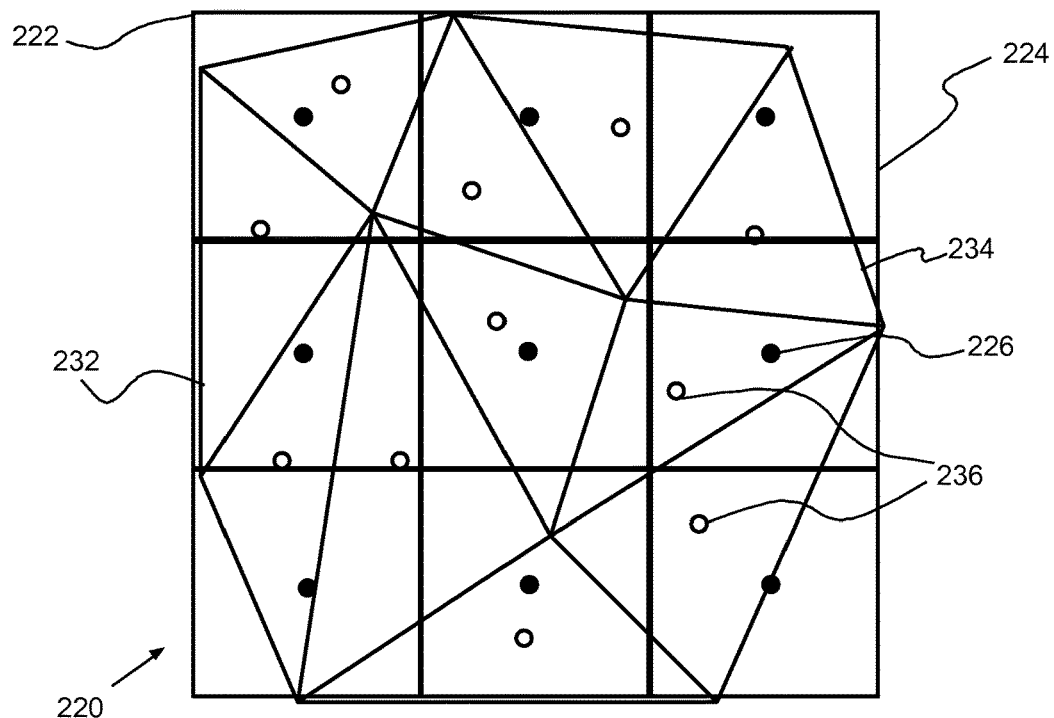
Figure 3C:
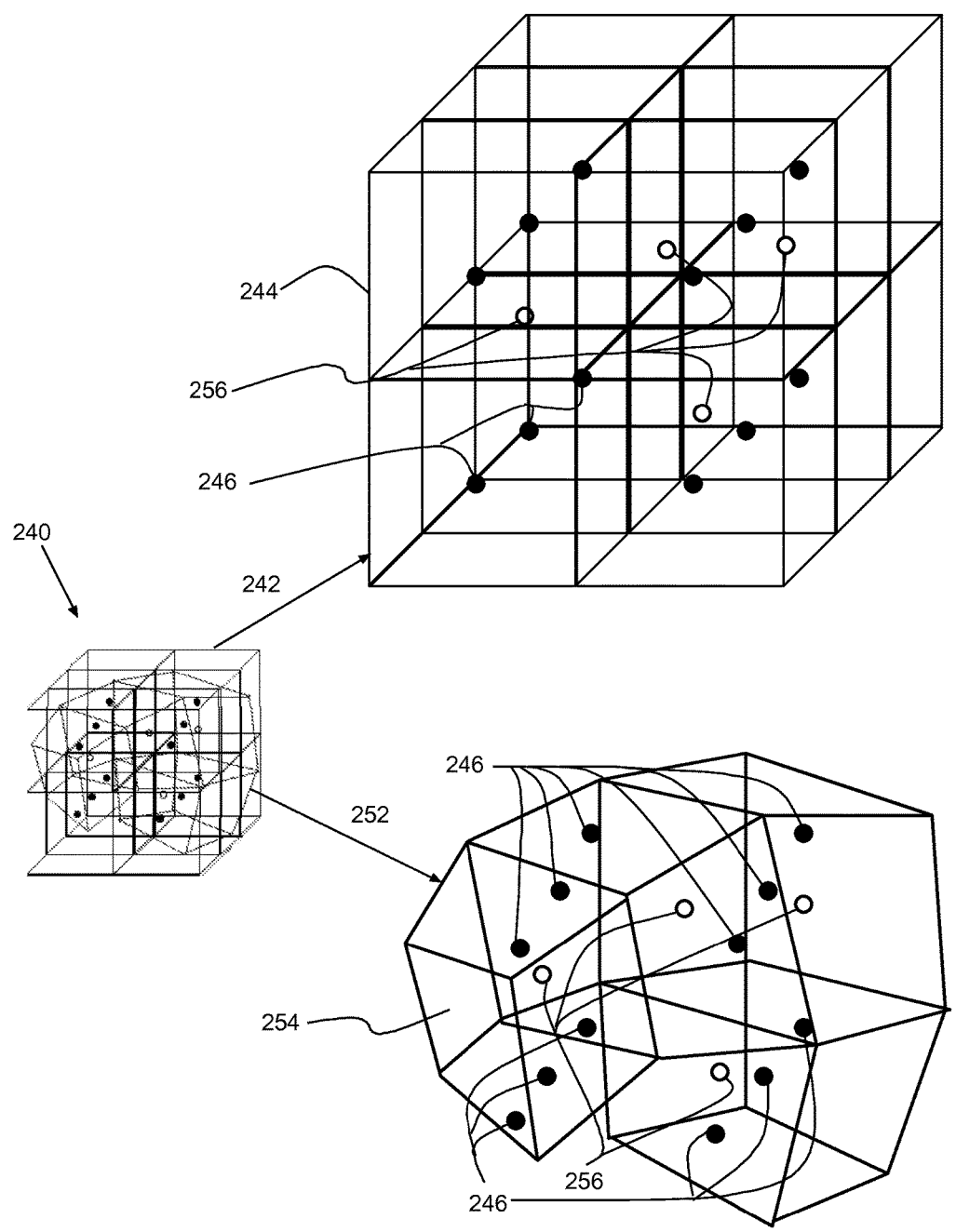
Figure 3D:
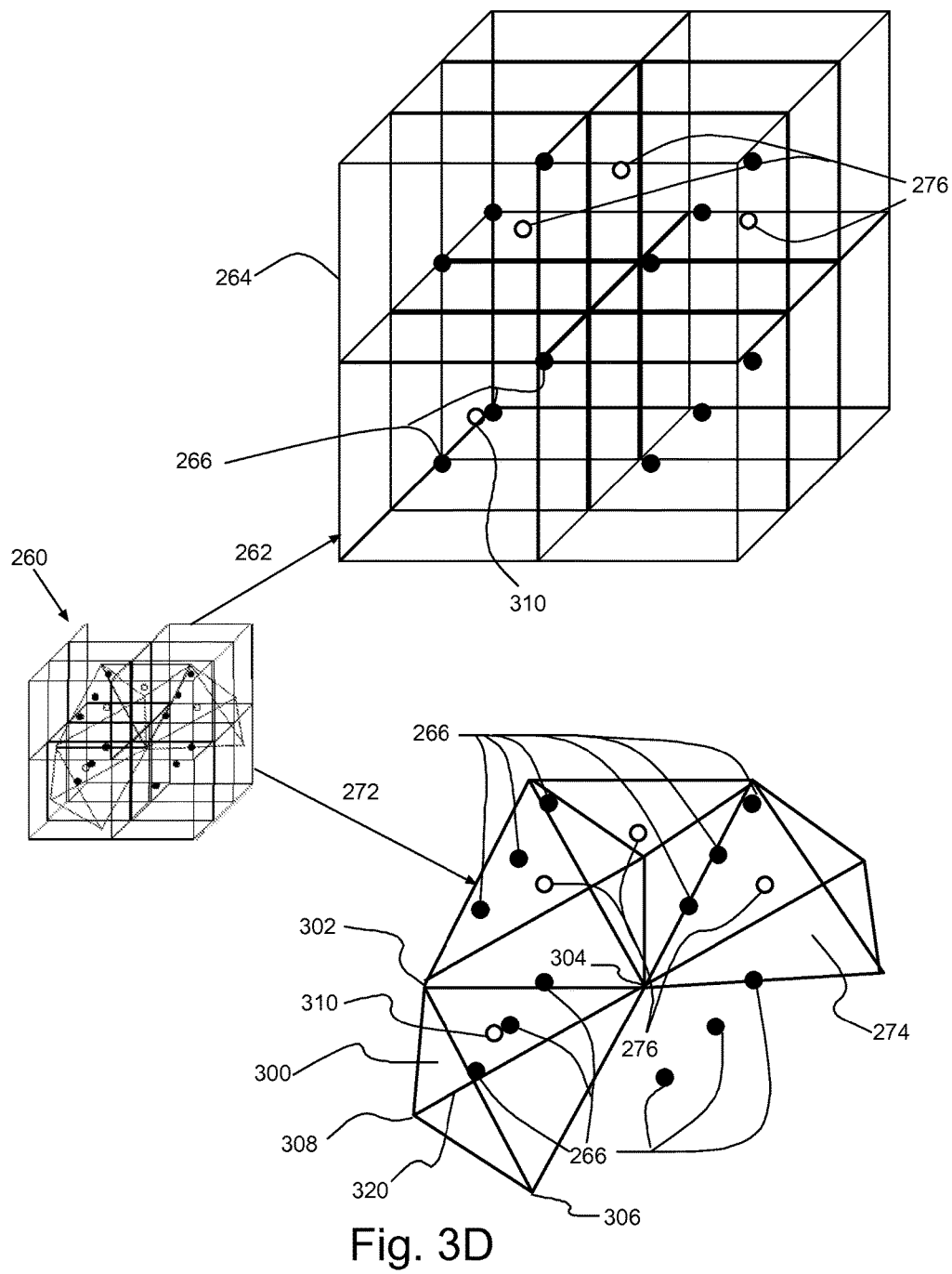
Figure 4:
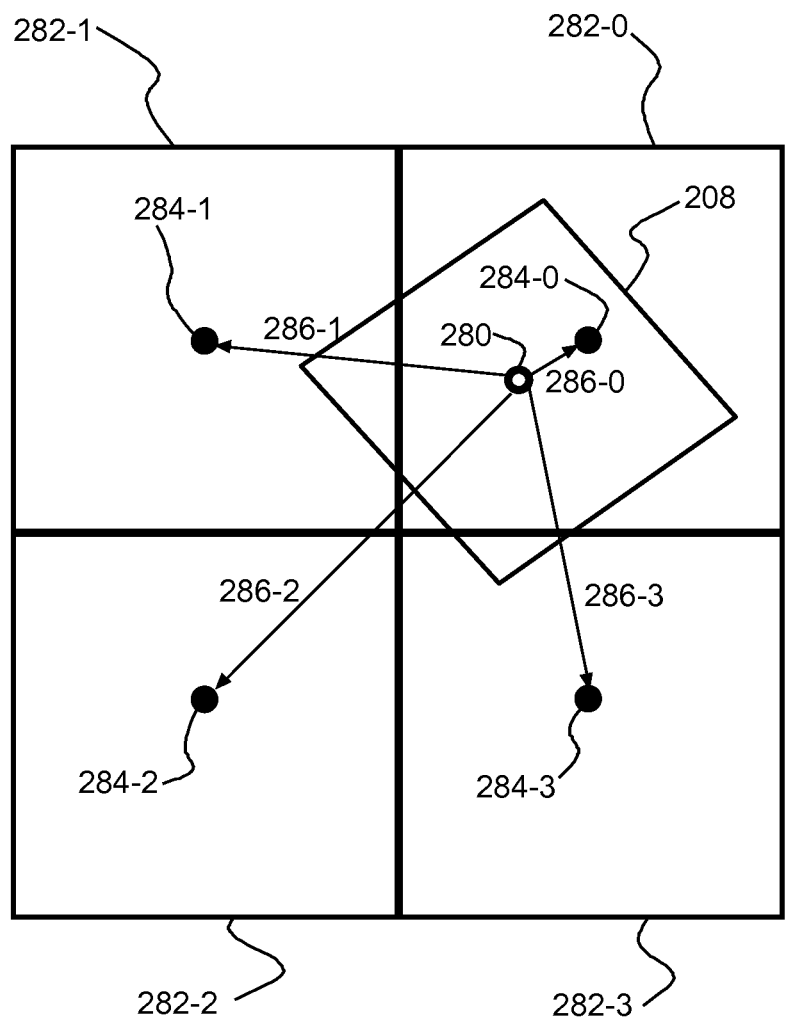
FIG. 4 shows an example of identifying n FVM cells completely, or partially, overlapping a single FEM element, the center 2D FEM element.

FIG. 4 shows an example of identifying 134 n FVM cells completely, or partially, overlapping a single FEM element 208 the center 2D FEM element in FIG. 3A. It should be noted that although described with reference to the 2D models for clarity and simplicity of explanation, the description has application to 3D cells as well, e.g., the examples in FIGS. 3C and 3D. In this example, FEM element 208 with centroid 280 overlaps four (n=4) FVM cells 282-0, 282-1, 282-2, 282-3, each with respective centroid 284-0, 284-1, 284-2, 284-3. Once identified, the system determines 136 the distance ($d_i$) 286-0, 286-1, 286-2, 286-3 between overlapped FVM cell centroids 284-0, 284-1, 284-2, 284-3 and the centroid 280 of the respective FEM element 208.

The system 100 determines 138 FVM cell contribution components in the FEM element 208 for each cell. Each overlapped FVM cells 282-0, 282-1, 282-2, 282-3 contributes a pore pressure $P_i$ component and diagonal permeability tensor, determined at the cell centroid 280 for each FEM element 208. From these components the system 100 determines a FEM element 208 permeability norm $\|k_i\|$ for each FEM element. The system 100 also maps 140 fluid characteristics to FEM element centroids 280 for each FEM element. The system 100 may map pressure $P_K^c$ and the permeability norm $\|k_K^c\|$ for each FEM centroid relating the particular FEM centroid 280 to the FVM centroids 284-0, 284-1, 284-2, 284-3. For example, a typical inverse-distance weighted approach is described in Lam, N. S-N. *Spatial Interpolation Methods: A Review. Cartography and Geographic Information Science*, pp. 129-150, 1983. As described in Lam, $$P_K^c = \frac{\sum_{i=1}^{n} P_i/d_i}{\sum_{i=1}^{n} 1/d_i}$$

$$\|k_K^c\| = \frac{\sum_{i=1}^{n} \|k_i\|/d_i}{\sum_{i=1}^{n} 1/d_i}$$

$$\|\lambda_K^c\| = \frac{\sum_{i=1}^{n} \|\lambda_i\|/d_i}{\sum_{i=1}^{n} 1/d_i}$$

$$T_K^c = \frac{\sum_{i=1}^{n} T_i/d_i}{\sum_{i=1}^{n} 1/d_i}.$$

Figure 5:
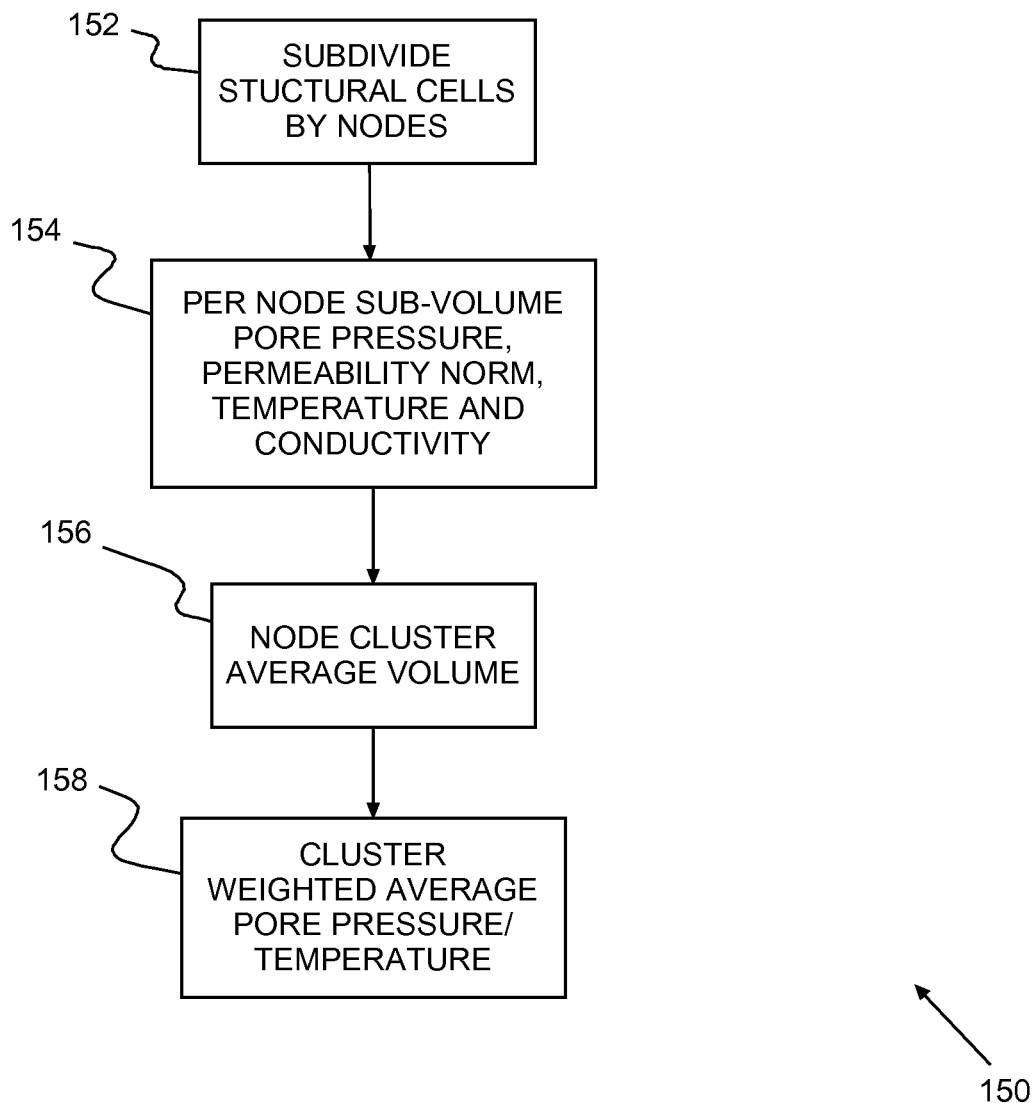
FIG. 5 shows an example of projecting volume average pore pressure and temperature across each FEM element, weighted by sub-volume permeability and conductivity respectively.

FIG. 5 shows an example of projecting 150 in inverse volume average pore pressure and temperature to FEM element nodes, weighted by inverse sub-volume permeability and conductivity. This begins by dividing 152 each FEM element into sub-volumes, one sub-volume for each element node. Then, the system 100 associates 154 each element node with corresponding characteristics/volumetric parameters at the respective element centroid. After segmenting all FEM elements, each node is surrounded by a cluster of sub-volumes. The system 100 averages 156 the inverse volume of neighboring sub-volumes for each FEM mesh node. Finally, the system 100 averages 158 pore pressure and temperature weighted by sub-volume and determines the permeability/conductivity norm at each element node, where the conductivity norm, in an embodiment of the invention may be calculated as $\|\lambda\|=\sqrt{(\lambda_{xx})^2+(\lambda_{yy})^2+(\lambda_{zz})^2}$.

Figure 6A:
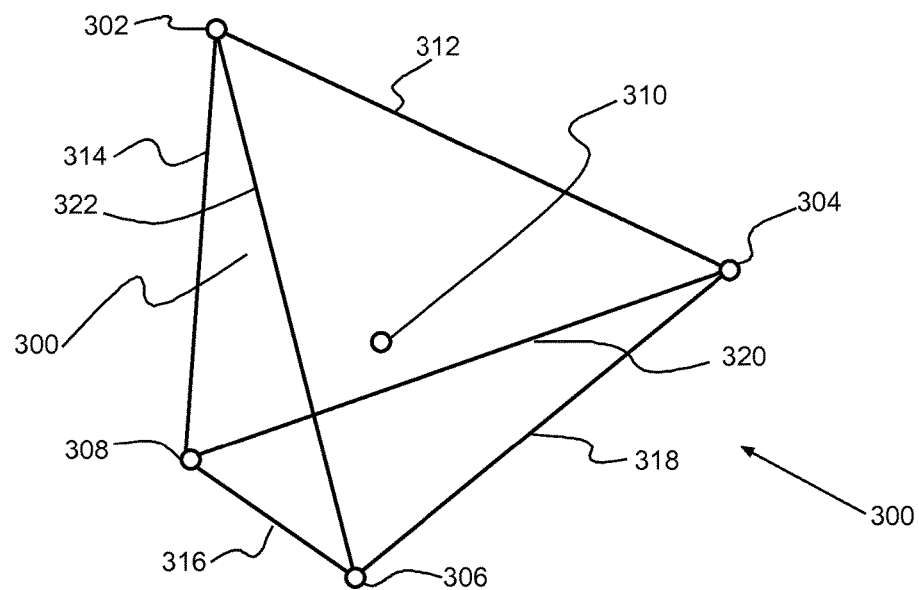
FIGS. 6A-B show an example of dividing tetrahedral shaped FEM elements into sub-volumes.
Figure 6B:
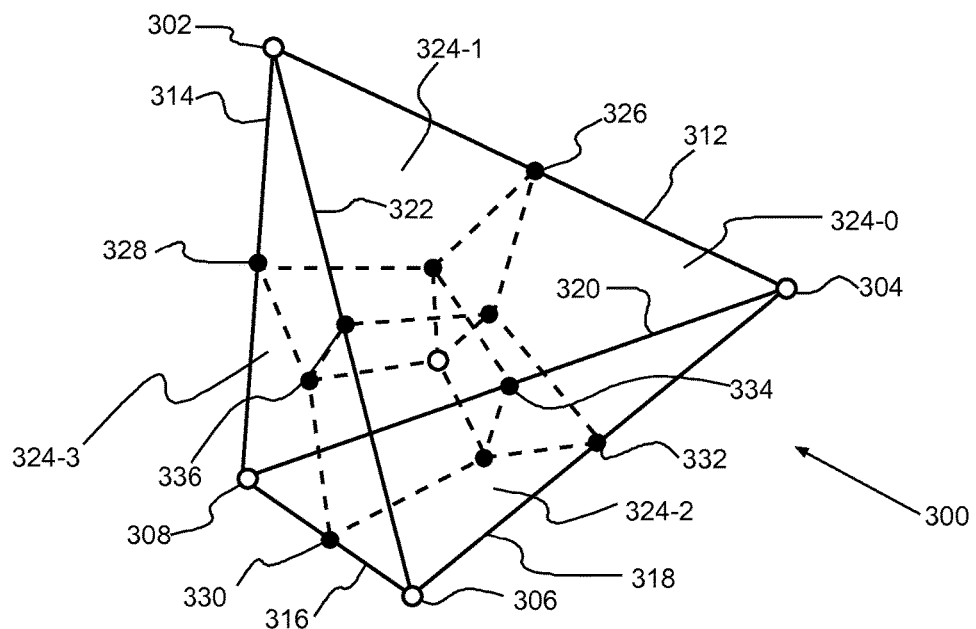

FIGS. 6A-B show an example of dividing 152 tetrahedral shaped FEM elements 300 into sub-volumes, e.g., element 300 in FIG. 3D. The tetrahedral shaped element 300 includes 4 nodes 302, 304, 306, 308, centroid 310 ($P_K^c$, $\|k_K^c\|$) and 6 edges 312, 314, 316, 318, 320, 322 defining 4 sides. In the example of FIG. 3D element nodes 302 and 304 are common nodes with an adjacent element, which also shares edge 320. For each node 302, 304, 306, 308 the system 100 defines 152 a sub-volume ($V_K$) 324-0, 324-1, 324-2, 324-3 that terminates on centroid 310. Edge 312, 314, 316, 318, 320, 322 midpoints 326, 328, 330, 332, 334, 336 are sub-volume 324-0, 324-1, 324-2, 324-3 nodes, each at one end of a sub-edge, opposite an associated element node 302, 304, 306, 308 or the centroid 310.

Figure 7A:
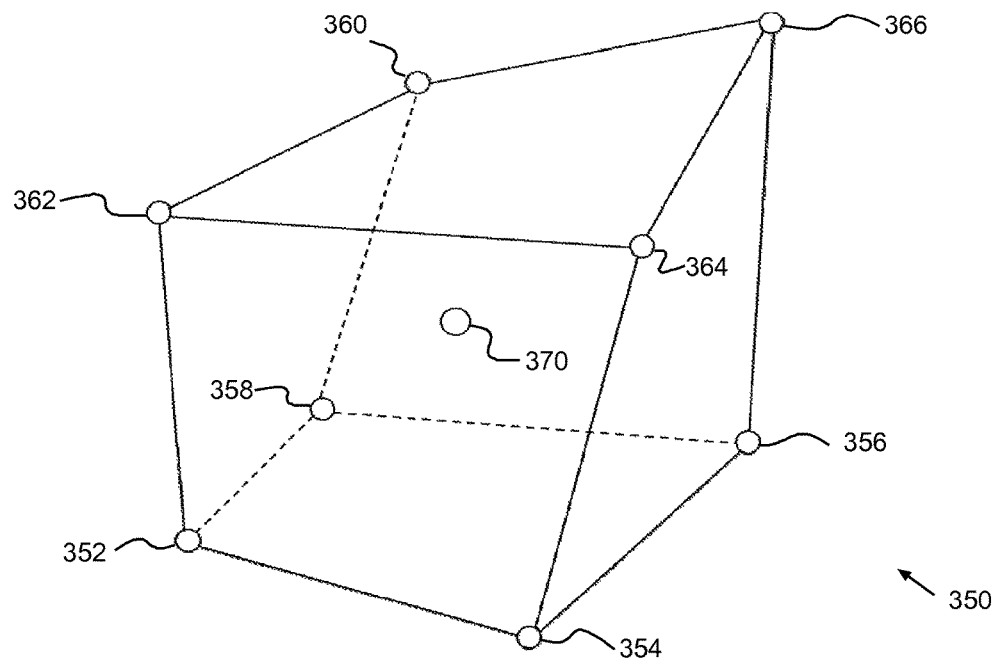
FIGS. 7A-B show an example of dividing irregularly shaped hexahedron FEM elements into sub-volumes.
Figure 7B:
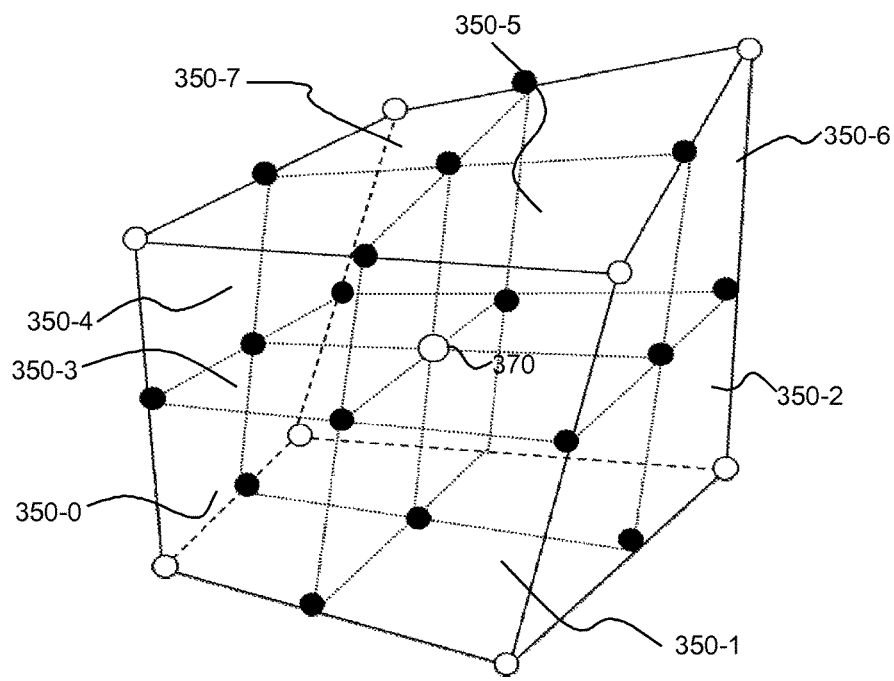

FIGS. 7A-B show an example of dividing 152 irregularly shaped hexahedron FEM elements into sub-volumes for tetrahedral shaped elements 350, e.g., cells 254 in FIG. 3C. The irregularly shaped hexahedron cells 350 each include 8 nodes 352, 354, 356, 358, 360, 362, 364, 366, centroid 370, and 12 edges defining 6 sides. Again, for each node 352, 354, 356, 358, 360, 362, 364, 366, the system 100 defines 152 a sub-volume 350-0, 350-1, 350-2, 350-3, 350-4, 350-5, 350-6, 350-7, that terminates on the centroid 370. Edge midpoints are sub-volume 350-0, 350-1, 350-2, 350-3, 350-4, 350-5, 350-6, 350-7 nodes, each at one end of a sub-edge, opposite an associated element node 352, 354, 356, 358, 360, 362, 364, 366, or the centroid 370.

After defining 152 sub-volumes 324-0, 324-1, 324-2, 324-3, or 350-0, 350-1, 350-2, 350-3, 350-4, 350-5, 350-6, 350-7 for all FEM elements 300, 350, the system 100 associates 154 each element node with corresponding characteristics/volumetric parameters. For example with regard to FIG. 6B, the system 100 may associate 154 the defined sub-volumes ($V_k$) 324-0, 324-1, 324-2, 324-3, pore pressures $P_K$, permeability norm $\|k_K^c\|$, temperature $T_K^c$ and conductivity $\|\lambda_K^c\|$ with the respective nodes 302, 304, 306, 308; and with regard to FIG. 7B, the defined sub-volumes ($V_K$) 350-0, 350-1, 350-2, 350-3, 350-4, 350-5, 350-6, 350-7, pore pressures $P_K^c$, permeability norm $\|k_K^c\|$, temperature $T_K^c$ and conductivity $\|\lambda_K^c\|$ with the respective nodes 352, 354, 356, 358, 360, 362, 364, 366.

Figure 8:
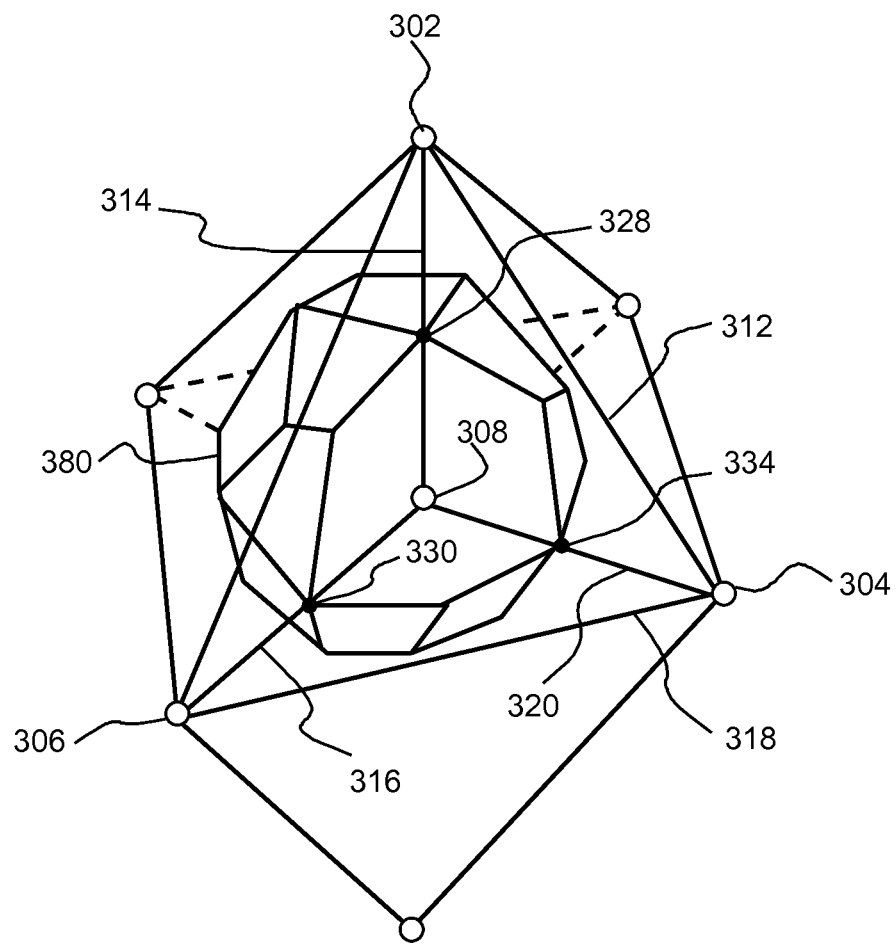
FIG. 8 shows an example of a cluster of sub-volumes around a single common node (not shown) shared with adjacent FEM elements.

FIG. 8 shows an example of a cluster 380 of sub-volumes around a single common node 308 shared with adjacent FEM elements. Each such common node (j), e.g., nodes 302 and 304 in FIGS. 6A-B, is a node in multiple sub-volumes. Thus, each node j has an associated sub-volume $V_K$ in multiple elements $K \in \tau_j$, where $\tau_j$ is the set of element indices sharing node/vertex j. The system assembles adjacent sub-volume clusters 380, clustered around each such common node. For each FEM node cluster the system 100 averages 156 the inverse volume of neighboring sub-volumes ($1/V_K$) of each cluster 380. Thus, $\|k_K^c\|/\|k_K^c\|$ provides the permeability/conductivity norm of the respective sub-volume.

For each element, the system 100 averages 158 pore pressure/temperature weighted by inverse sub-volume and the permeability/conductivity norm for each node. The final pore pressure/temperature ($P^j/T^j$) at each mesh node (j) is determined by $$P^j = \frac{\sum_{K \in \tau_j} P_K^c \|k_K^c\|/V_K}{\sum_{K \in \tau_j} \|k_K^c\|/V_K}$$

$$T^j = \frac{\sum_{K \in \tau_j} T_K^c \|\lambda_K^c\|/V_K}{\sum_{K \in \tau_j} \|\lambda_K^c\|/V_K}.$$

It should be noted that fluid flow problem solutions tend to be less accurate in low permeability regions than in high permeability regions. Further, the reservoir may include totally impermeable regions that require defining a minimum value or lower limit for the permeability field at the respective cells/regions to insure convergence. Typical results in these low permeability regions are inaccurate when methods according to the prior art are used and frequently lead to otherwise unrealistic results. Thus, one may use a permeability field norm as weighting factor in determining nodal pressure, more heavily weighting, pressure cell values of high permeability regions. So, the system 100 also determines centroid pore pressures/Temperatures ($P_K^c/T_K^c$) from cell volume average weighted permeability/conductivity norms.

Also at reservoir boundaries, the system 100 may impose appropriate boundary conditions for pore pressure, e.g., through ghost cells imposing the desired conditions. Typical boundary conditions correspond to a no flow condition or a specified net flow.

Advantageously, the preferred system 100 facilitates data mapping between FEM and FVM models for reservoirs, seamlessly transferring fluid parameters from reservoir FVM centroids to FEM centroids for two different cell geometries. Preferably, data mapping is weighted with two weighting factors, a petrophysical weighting factor and a beta weighting factor, e.g., an inverse volume beta weighting factor. Alternately, the beta weighting factor could be an inverse distance beta weighting factor or a volume average beta weighting factor.

Further, the present invention reduces production analysis by limiting requisite analysis to those FVM cells in a reservoir FVM grid that overlap reservoir FEM elements. Thus having identified and reduced the FVM cells considered for production, the preferred system uses an inverse-distance weighted averaging to characterize the reservoir. Further, rather than requiring a linear system solution for the entire reservoir, the present invention arrives at a local projection from the center nodes. In addition, instead of transferring data between reservoir fluid and geomechanical projections, coupling values based only in geometric parameters and mathematical formulations, the present invention incorporates petrophysical parameters in coupling geometric modeling results for more realistic results.

While the invention has been described in terms of preferred embodiments, those skilled in the art will recognize that the invention can be practiced with modification within the spirit and scope of the appended claims. It is intended that all such variations and modifications fall within the scope of the appended claims. Examples and drawings are, accordingly, to be regarded as illustrative rather than restrictive.

What is claimed is:

1. A method of managing hydrocarbon field production, said method comprising:

modeling fluid properties of a hydrocarbon field in a finite volume method (FVM) model and geomechanical properties in a finite element method (FEM) model;

mapping model centroids to one another between FVM model cells and FEM model elements, wherein mapping model centroids comprises:

locating centroids in each FVM cell and each FEM element, identifying for said each FEM element every overlapping FVM cell, determining the distance ($d_i$) from the respective centroid for each identified said overlapping FVM cell to the respective overlapped FEM element centroid, determining overlapping FVM cell centroid pore pressure ($P_i$), permeability norm ($\|k_i\|$), conductivity $\|\lambda_i\|$ and temperature ($T_i$), and determining overlapped FEM element centroid pore pressure, permeability norm, conductivity norm and temperature, weighted inversely for distance between the respective centroids;

determining fluid characteristics in said each FEM element responsive to geomechanical FEM model characteristics for a coupled FVM-FEM model; and adjusting field production to extract field resources responsive to said coupled FVM-FEM model wherein requisite production analysis is reduced to FVM cells that overlap FEM elements.

2. A method of managing hydrocarbon field production as in claim 1, wherein said FVM model includes a plurality of FVM cells modeling fluid properties of said hydrocarbon field and said FEM model includes a plurality of FEM elements modeling geomechanical properties of said hydrocarbon field.

3. A method of managing hydrocarbon field production as in claim 2, wherein mapping model centroids maps fluid properties inverse-distance weighted from FVM cell centroids to FEM element centroids in coupling physical parameters with geometric properties.

4. A method of managing hydrocarbon field production as in claim 2, wherein determining fluid characteristics comprises:

segmenting each overlapped FEM element into a plurality of inverse sub-volumes ($V_K$), one sub-volume for each FEM element node; and determining a weighted average pore pressure and temperature of sub-volumes ($V_K$) clustered around said each FEM element node.

5. A method of managing hydrocarbon field production as in claim 4, wherein said weighted average pore pressure ($P^j$) and temperature ($T^j$) are determined from $$P^j = \frac{\sum_{K \in \tau_j} \frac{P_K^c \|k_K^c\|}{V_K}}{\sum_{K \in \tau_j} \frac{\|k_K^c\|}{V_K}}$$

$$T^j = \frac{\sum_{K \in \tau_j} \frac{T_K^c \|\lambda_K^c\|}{V_K}}{\sum_{K \in \tau_j} \frac{\|\lambda_K^c\|}{V_K}}$$

wherein $\tau_j$ is the set of element indices sharing node/vertex j.

6. A method of managing hydrocarbon field production as in claim 4, wherein said hydrocarbon field is a petro-chemical reservoir and said weighted average indicates petro-chemical volumetric properties at respective FEM element node locations in said petro-chemical reservoir.

7. A method of managing hydrocarbon field production as in claim 1, wherein pore pressure ($P_K^c$), permeability norm ($\|k_K^c\|$), conductivity norm ($\|\lambda_K^c\|$) and temperature ($T_K^c$) in the FEM element centroid are determined from $$P_K^c = \frac{\sum_{i=1}^{n} P_i / d_i}{\sum_{i=1}^{n} 1 / d_i}$$

$$\|k_K^c\| = \frac{\sum_{i=1}^{n} \|k_i\| / d_i}{\sum_{i=1}^{n} 1 / d_i}$$

$$\|\lambda_K^c\| = \frac{\sum_{i=1}^{n} \|\lambda_i\| / d_i}{\sum_{i=1}^{n} 1 / d_i}$$

$$T_K^c = \frac{\sum_{1}^{n} T_i / d_i}{\sum_{i=1}^{n} 1 / d_i}.$$

8. A method of managing hydrocarbon field production as in claim 1, wherein in any FVM cell having a permeability below a selected minimum, permeability is set to said selected minimum.

9. A method of managing petro-chemical reservoir production, said method comprising:

modeling a hydrocarbon field in a finite volume method (FVM) model including a plurality of FVM cells;

modeling a hydrocarbon field in a finite element method (FEM) model including a plurality of FEM elements;

locating centroids in each FVM cell and each FEM element;

identifying for said each FEM element every overlapping FVM cell;

determining the distance ($d_i$) from the respective centroid for each identified said overlapping FVM cell to the respective overlapped FEM element centroid;

determining overlapping FVM cell centroid pore pressure ($P_i$), permeability norm ($\|k_i\|$) and temperature ($T_i$);

determining overlapped FEM element centroid pore pressure ($P_K^c$), permeability norm ($\|k_K^c\|$), conductivity norm ($\|\lambda_K^c\|$) and temperature ($T_K^c$) weighted inversely for distance between the respective centroids;

segmenting each overlapped FEM element into a plurality of sub-volumes ($V_K$), one sub-volume for each FEM element node;

determining a weighted average pore pressure ($P^j$) and temperature ($T^j$) of sub-volumes ($V_K$) clustered around said each FEM element node for a coupled FVM-FEM model coupling physical parameters with geometric properties; and adjusting field production to extract field resources responsive to said coupled FVM-FEM model wherein requisite production analysis is reduced to FVM cells that overlap FEM elements.

10. A method of hydrocarbon field production as in claim 9, wherein pore pressure ($P_K^c$), permeability norm ($\|k_K^c\|$), conductivity norm ($\|\lambda_K^c\|$) and temperature ($T_K^c$) are determined from $$P_K^c = \frac{\sum_{i=1}^{n} P_i / d_i}{\sum_{i=1}^{n} 1/d_i}$$

$$\|k_K^c\| = \frac{\sum_{i=1}^{n} \|k_i\| / d_i}{\sum_{i=1}^{n} 1/d_i}$$

$$\|\lambda_K^c\| = \frac{\sum_{i=1}^{n} \|\lambda_i\| / d_i}{\sum_{i=1}^{n} 1/d_i}$$

$$T_K^c = \frac{\sum_{i=1}^{n} T_i / d_i}{\sum_{i=1}^{n} 1/d_i}.$$

11. A method of hydrocarbon field production as in claim 10, wherein in any FVM cell having a permeability below a selected minimum, permeability is set to said selected minimum, and said weighted average pore pressure ($P^j$) and temperature ($T^j$) are determined from $$P^j = \frac{\sum_{K \in \tau_j} \frac{P_K^c \|k_K^c\|}{V_K}}{\sum_{K \in \tau_j} \frac{\|k_K^c\|}{V_K}}$$

$$T^j = \frac{\sum_{K \in \tau_j} \frac{T_K^c \|\lambda_K^c\|}{V_K}}{\sum_{K \in \tau_j} \frac{\|\lambda_K^c\|}{V_K}}.$$

\* \* \* \* \*